US012636067B2

(12) United States Patent (10) Patent No.: US 12,636,067 B2
Koon et al. (45) Date of Patent: May 26, 2026

(54) METHOD FOR DETERMINING PUNCTURE ENTRY LOCATION USING ELECTROANATOMIC MAPPING

(71) Applicant: Boston Scientific Medical Device Limited, Galway (IE)

(72) Inventors: Lauren Koon, Mississauga (CA); Charlene Leung, Scarborough (CA)

(73) Assignee: Boston Scientific Medical Device Limited, Galway (IE)

( * ) Notice: Subject to any disclaimer, the term of this patent is extended or adjusted under 35 U.S.C. 154(b) by 322 days.

(21) Appl. No.: 18/361,007

(22) Filed: Jul. 28, 2023

(65) Prior Publication Data

US 2024/0032985 A1 Feb. 1, 2024

Related U.S. Application Data

(60) Provisional application No. 63/369,691, filed on Jul. 28, 2022.

(51) Int. Cl.
*A61B 18/14* (2006.01)
*A61M 29/02* (2006.01)
*A61B 18/00* (2006.01)

(52) U.S. Cl.
CPC ............. *A61B 18/14* (2013.01); *A61M 29/02* (2013.01); *A61B 2018/00351* (2013.01); *A61B 2018/00601* (2013.01); *A61B 2018/00875*

(2013.01); *A61B 2018/00892* (2013.01); *A61B 2018/1425* (2013.01); *A61M 2029/025* (2013.01)

(58) Field of Classification Search
CPC . A61B 18/14; A61B 18/1477; A61B 18/1492; A61B 2018/00351; A61B 2018/00357; A61B 2018/00363; A61B 2018/00386; A61B 2018/00601; A61B 2018/00839; A61B 2018/00875; A61B 2018/00892; A61B 2018/1425; A61B 2018/144; A61M 29/02; A61M 2029/025
See application file for complete search history.

(56) References Cited

U.S. PATENT DOCUMENTS

2019/0343579 A1* 11/2019 Tandri ................ A61B 18/1815
2020/0008883 A1* 1/2020 Moak ..................... A61B 18/18
2021/0228268 A1* 7/2021 Urbanski ............... A61B 5/287

* cited by examiner

*Primary Examiner* — Khadijeh A Vahdat
(74) *Attorney, Agent, or Firm* — Nelson Mullins Riley & Scarborough LLP

(57) ABSTRACT

A method and apparatus are disclosed for puncturing and using the puncturing device to evaluate and identify the anatomical space that the puncturing device has entered. The physician can then determine if the puncturing device has entered the desired anatomical space or an unintended anatomical space.

20 Claims, 8 Drawing Sheets

METHOD FOR DETERMINING PUNCTURE ENTRY LOCATION USING ELECTROANATOMIC MAPPING

CROSS-REFERENCES TO RELATED APPLICATIONS

This application claims the benefit of U.S. Provisional Application No. 63/369,691, entitled "METHOD FOR DETERMINING PUNCTURE ENTRY LOCATION USING ELECTROANATOMIC MAPPING," and filed Jul. 28, 2022, which is hereby incorporated by reference in its entirety.

TECHNICAL FIELD

The disclosure relates to methods and devices for puncturing tissue. More specifically, it relates to methods and devices for increasing the safety of dilating a tissue puncture in and around a heart.

BACKGROUND OF THE ART

Interventionalists often create punctures to access different chambers or spaces within the body; for example, creating a transseptal puncture to reach the left atrium from the right atrium. Other examples include accessing ventricular chambers, pericardial space, etc. Specifically in the cardiovascular system, a puncture that is dilated to a larger hole size (e.g., larger than the diameter of a typical transseptal needle or mechanical guidewire) in the wrong location and which accesses an unintended space, may cause serious complication like hemopericardium. This adverse event can result in serious surgery, injury, or death. A puncture with a transseptal needle or wire is not likely to cause these major complications, but the step of dilation can cause massive hemopericardium.

In transseptal procedures, specifically procedures where ultrasound is not used, there are precautions taken to identify the site of puncture, prior to dilation. If the puncture is in the wrong space, the physician can back out with relatively mild consequences, if dilation has not occurred. For needle-based puncture workflow, it is standard practice to use pressure readings to identify the location of the needle tip. There are characteristic waveforms for the right atrium, left atrium, and aorta. An external medical pressure transducer is connected to the lumen of the needle via a luer connector at the proximal end.

Another method is to inject contrast through the lumen of the needle. This can help identify tenting of the fossa ovalis from a characteristic dome shape. But after puncture, the contrast can also be used to identify the accessed space based on the outline and direction of flow of contrast visualized on fluoroscopy.

Pressure readings with fluid medical transducers can be unreliable and prone to error with movement. Contrast is subject to limitations with patient selection and external factors. And contrast may be harmful to some patients with renal disease.

In addition, the use of pressure readings and contrast is not feasible with puncture devices that do not have a lumen. Adoption of a wire-based transseptal puncture platform can be challenged by the inability to use these techniques. Without the use of these techniques, the operator may not feel confident that they will dilate in the correct region.

SUMMARY

Example 1 is a method of puncturing a target tissue and evaluating an anatomical space. The method includes (a)

puncturing the target tissue with an elongate puncture device to create a puncture. The method includes (b) advancing a distal tip of the elongate puncture device through the puncture and into the anatomical space. Additionally, the method includes (c) evaluating a shape of the anatomical space using the elongate puncture device; and (d) identifying the anatomical space.

Example 2 is the method of Example 1, wherein step (c) includes using the distal tip of the elongate puncture device to evaluate the anatomical space.

Example 3 is the method of Example 1, further comprising a step (e) of withdrawing the elongate puncture device and repeating steps (a) to (d) until a desired anatomical space is identified.

Example 4 is the method of Example 1, further comprising a step (e), when a desired anatomical space is identified, of advancing a dilator over the elongate puncture device to dilate the puncture.

Example 5 is the method of Example 3, further comprising a step (f) of advancing a sheath.

Example 6 is the method of Example 1, wherein the elongate puncture device is a wire, a microcatheter, or a needle.

Example 7 is the method of Example 1, wherein the elongate puncture device has a sharp tip for mechanical puncturing.

Example 8 is the method of Example 1, wherein the elongate puncture device has an electrode for delivering electrical energy for puncturing.

Example 9 is the method of Example 1, wherein step (b) includes the elongate puncture device being electrically connected to an EAM system while the elongate puncture device is being advanced.

Example 10 is the method of Example 1, wherein the anatomical space is identified to be a left atrium, an aorta, a pericardial space, or a thoracic cavity which is extrapericardial.

Example 11 is a method of puncturing a target tissue and evaluating an anatomical space. The method includes (a) puncturing the target tissue with an elongate puncture device to create a puncture. The method includes (b) advancing a distal tip of the elongate puncture device through the puncture and into the anatomical space. The method also includes (c) evaluating a quality of the anatomical space using the elongate puncture device; and (d) identifying the anatomical space.

Example 12 is the method of Example 11, wherein the quality being evaluated is voltage or impedance.

Example 13 is the method of Example 11, wherein step (c) includes using the distal tip of the elongate puncture device to evaluate the anatomical space.

Example 14 is the method of Example 11, further comprising a step (e) of withdrawing the elongate puncture device and repeating steps (a) to (d) until a desired anatomical space is identified.

Example 15 is the method of Example 11, further comprising a step (e), when a desired anatomical space is identified, of advancing a dilator over the elongate puncture device to dilate the puncture.

Example 16 is the method of Example 11, further comprising a step (f) of advancing a sheath.

Example 17 is the method of Example 11, wherein the elongate puncture device is a wire, microcatheter, or needle.

Example 18 is the method of Example 11, wherein the elongate puncture device has a sharp tip for mechanical puncturing.

Example 19 is the method of Example 11, wherein the elongate puncture device has an electrode for delivering electrical energy for puncturing.

Example 20 is the method of Example 11, wherein the anatomical space is identified to be a left atrium, an aorta, a pericardial space, or a thoracic cavity which is extrapericardial.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
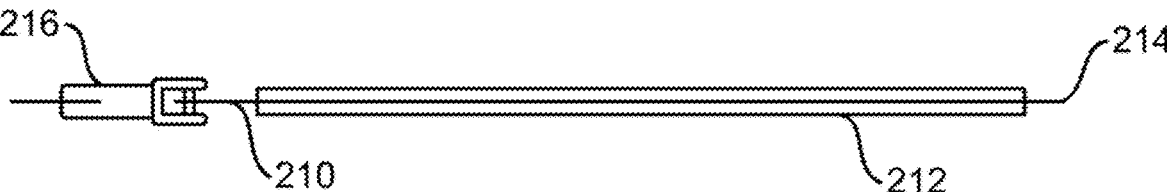
FIG. 1 is an illustration of a mechanical puncture wire with modular insulation.

The problem of dilating a puncture after the puncturing device has punctured tissue and entered an anatomical space which is a wrong anatomical space (i.e., not the intended anatomical space) can be addressed by using the puncturing device to evaluate and identify the anatomical space which the puncturing device has entered. The physician can then determine if the puncturing device has entered the desired anatomical space or a wrong anatomical space.

In a first broad aspect, embodiments of the present invention are for a method of puncturing a target tissue and evaluating an anatomical space, the method comprising the steps of: (a) puncturing the target tissue with an elongate puncture device to create a puncture; (b) advancing a distal tip of the elongate puncture device through the puncture and into the anatomical space; (c) evaluating a shape of the anatomical space using the elongate puncture device; and (d) identifying the anatomical space. In some embodiments, step (c) includes using the distal tip of the elongate puncture device to evaluate the anatomical space.

As a feature of the first broad aspect, some embodiments further comprise a step (e) of withdrawing the elongate puncture device and repeating steps (a) to (d) until a desired anatomical space is identified. Some embodiments further comprise a step (e), when a desired anatomical space is identified, of advancing a dilator over the elongate puncture device to dilate the puncture.

As a further feature of the first broad aspect, some embodiments further comprise a step (f) of advancing a sheath.

As further features of the first broad aspect, some embodiments further comprise the elongate puncture device is a wire, other embodiments comprise the elongate puncture device is a microcatheter, and further embodiments comprise the elongate puncture device is a needle. In some examples, the elongate puncture device has a sharp tip for mechanical puncturing, and in other examples, the elongate puncture device has an electrode for delivering electrical energy for puncturing.

In some embodiments, step (b) includes the elongate puncture device being electrically connected to an electro-anatomic mapping (EAM) system while the elongate puncture device is being advanced.

Embodiments of the first broad aspect include the anatomical space being identified to be a left atrium, or an aorta, or a pericardial space, or a thoracic cavity which is extrapericardial.

In a second broad aspect, embodiments of the present invention are for a method of puncturing a target tissue and evaluating an anatomical space, the method comprising the steps of: (a) puncturing the target tissue with an elongate puncture device to create a puncture; (b) advancing a distal tip of the elongate puncture device through the puncture and into the anatomical space; (c) evaluating a quality of the anatomical space using the elongate puncture device; and (d) identifying the anatomical space. In some embodiments, the quality being evaluated is voltage, and in other embodiments, the quality being evaluated is impedance. In some embodiments, step (c) includes using the distal tip of the elongate puncture device to evaluate the anatomical space.

As a feature of the second broad aspect, some embodiments further comprise a step (e) of withdrawing the elongate puncture device and repeating steps (a) to (d) until a desired anatomical space is identified. Some embodiments further comprise a step (e), when a desired anatomical space is identified, of advancing a dilator over the elongate puncture device to dilate the puncture. Some embodiments further comprising a step (f) of advancing a sheath.

As further features of the second broad aspect, embodiments include the elongate puncture device being a wire, or a microcatheter, or a needle. In some examples, the elongate puncture device has a sharp tip for mechanical puncturing, and in other examples, the elongate puncture device has an electrode for delivering electrical energy for puncturing.

Embodiments of the second broad aspect include the anatomical space being identified to be a left atrium, an aorta, a pericardial space, or a thoracic cavity which is extrapericardial.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

There is a need for interventionalists to create punctures to access different chambers or spaces within the body; for example, creating a transseptal puncture to reach the left atrium from the right atrium. Other examples include accessing ventricular chambers, pericardial space, etc. Specifically in the cardiovascular system, a puncture that is dilated to a larger hole size (e.g., larger than the diameter of a typical transseptal needle or mechanical guidewire) in the wrong location and which accesses an unintended space, may cause serious complication like hemopericardium. This adverse event can result in serious surgery, injury, or death. A puncture with a transseptal needle or wire is not likely to cause these major complications, but the step of dilation can cause massive hemopericardium.

In transseptal procedures, specifically procedures where ultrasound is not used, there are precautions taken to identify the site of puncture, prior to dilation. If the puncture is in the wrong space, the physician can back out with relatively mild consequences, if dilation has not occurred. For needle-based puncture workflow, it is standard practice to use pressure readings to identify the location of the needle tip. There are characteristic waveforms for the right atrium, left atrium, and aorta. An external medical pressure transducer is connected to the lumen of the needle via a luer connector at the proximal end.

Another method is to inject contrast through the lumen of the needle. This can help identify tenting of the fossa ovalis from a characteristic dome shape. But after puncture, the contrast can also be used to identify the accessed space based on the outline and direction of flow of contrast visualized on fluoroscopy.

Pressure readings with fluid medical transducers can be unreliable and prone to error with movement. Contrast is subject to limitations with patient selection and external factors. And contrast may be harmful to some patients with renal disease.

In addition, the use of pressure readings and contrast is not feasible with puncture devices that do not have a lumen. Adoption of a wire-based transseptal puncture platform can be challenged by the inability to use these techniques. Without the use of these techniques, the operator may not feel confident that they will dilate in the correct region.

Disclosed herein is a method of identifying a newly accessed space after puncture with a wire-based platform, and therefore identifying the risk of dilating the puncture site. This method uses characteristics of the wire and the integration of the puncture wire with an electroanatomical mapping system. The method utilizes the anatomical constraints imposed by tissue bodies on the wire, and physiological characteristics of the tissue.

One workflow in accordance with the method includes the following steps: (1) Puncturing a tissue barrier from a known space, into an unknown space, using a small profile device, e.g., needle or wire.

(2) Feeding a wire into the space. This wire may be the device used for puncturing, or a separate device using the initial puncture hole for access. The wire is meant to be low profile, such that advancement of the wire will not cause hemodynamic complications if removed.

(3) Using the wire in conjunction with the EAM system to determine the location of the wire and qualities of the newly accessed space.

(4) Once determined that the newly accessed space is sufficiently safe to dilate into (i.e., the originally targeted space), a dilating device may be tracked over the wire to dilate the tissue in between the two spaces.

(5) A sheath may be tracked over the dilator for access, and extraneous devices may be removed for additional steps in the procedure.

With a 3D visualization of the chamber/space of origin from fast anatomical mapping (FAM) or voltage mapping on the EAM system, the initial positioning and trajectory of the puncture device can be determined with multiple views.

Description of the Wire Device

The device entering the new chamber or space for the purpose of identifying whether or not it is safe to dilate may be a microcatheter, an RF wire, or a guidewire, or some other wire. The term wire is used herein to indicate a flexible elongate device and is not intended to restrict the materials comprising the wire or flexible elongate device. The device must be low profile such that it does not create a hole size large enough to cause hemodynamic consequence as it advances, and it must also be able back out of the puncture site without causing dilation leading to significant hemodynamic consequence. Some embodiments of the wire device include a tip and distal body with outer diameters of less than 0.035 inches.

In an embodiment where the wire serves as a puncture device, the distal tip of the wire may either be sharp for mechanical puncture of tissue, or it may have an electrode to apply energy to the tissue for puncture. The electrode for puncture may also be visualizable on an EAM system by connecting the electrode to the EAM system with a connecting device. Such connecting device may be, for example, a DuoMode™ cable available from Baylis Medical Company, Inc. which is a cable that streamlines the connection between an NRG® Transseptal Needle, an EAM, and the Baylis RF Puncture Generator. Alternatively, the tip of a mechanical puncture wire may also serve as a conductive electrode for connection to the EAM system. For both embodiments, the exposed metal electrode is preferably limited in surface area (i.e., the whole wire should not be exposed in the blood pool/space) for device location specificity.

For a mechanical puncture wire 210, the tip electrode is not required for the puncture step. Thus, the insulation 212 may be fixed, or modular to adjust the exposed length (FIG. 1). FIG. 1 illustrates a conductive mechanical puncture wire 210 with modular insulation 212 in retracted position to allow for a distal mechanism to perform puncture. The mechanical puncture wire 210 has a mechanical puncture feature 214 at the distal tip of the wire. An example of this modular insulation may be a microcatheter. Optionally, there may be a mechanism to lock the insulation in place with respect to the conductive wire.

For a device to be tracked over the mechanical puncture wire 210, mechanical puncture wire 210 has a removable handle 216 that electrically connects the electrode to the puncture and/or EAM system. In alternative embodiments, the devices are pre-loaded. Some examples of preloading include the sheath and dilator being loaded onto the proximal portion of the wire, and then the distal portion of the wire, without the sheath and dilator, being inserted into the patient. This would require the wire to have sufficient length if a dilator or sheath is pre-loaded.

The wire device should be atraumatic such that when unconstrained and deployed into the new space after puncture, the device should not injure tissue. This may be achieved by an atraumatic tip and/or a shape that would make tissue contact with the tip unlikely (for example, a spiral or 3D spiral configuration with the tip at the center). In other words, some alternative embodiments have a curved distal shape or configuration such that a sharp tip (or even a distal tip) does not contact tissue.

The wire device should have at least one electrode but may include a plurality of electrodes visualizable on an EAM system. These electrodes may also be optionally connected to a system to read electrograms (EGMs) or heart pace.

In some alternative embodiments, a needle is used for puncturing, a wire is fed through the lumen of the needle, and the needle is withdrawn.

Three Embodiments for Evaluation of Newly Accessed Space

Disclosed herein are three embodiments for the evaluation of newly accessed space: (1) Wire trajectory in free unmapped space; (2) Mapping the new space; and (3) General impedance (may be EAM system or other system, e.g., generator software). The second embodiment of Mapping new space includes (a) Fast anatomical mapping (FAM) and (b) voltage/activation mapping.

The above embodiments may be used together or independently to gather information about the new space, and the safety of advancing the dilator. Table 1 below provides examples of different characteristics exemplary of a variety of anatomical spaces in or near the heart.

Right atrium 102 is previously mapped so it is visible on the EAM system. The portions of the inferior vena cava 112 and superior vena cava 114 adjacent to right atrium 102 may also be mapped.

The tissue surrounding the left atrium 100, left ventricle 108, and right ventricle 110 are not visible on the EAM system until the tissue is mapped.

TABLE 1

| | Anatomical space | | | | |
|---|---|---|---|---|---|
| Method | Right Atrium | Left Atrium | Aorta | Pericardial Space | Thoracic Cavity (Extrapericardial) |
| Trajectory | Travels within RA map (assumed reference) | To right of RA landmarks (LAO), limited by RA space (4 cm 1) (wire prolapse) | Anterior and superior travel (ascending aorta); or anterior and inferior (left ventricle, if able to pass aortic cusps) | Travels in arc around heart silhouette | Travels around mediastinum, between heart and lung profiles, or between lung and diaphragm |
| Map creation (mapped volume from FAM and voltage map) | Connected to vena cava, characteristic structure, may be initially mapped for reference | Characteristic PVs, chamber approximately 4 cm across 1, to the right (LAO) of the right atrium | Vertical tube (aorta), or left ventricle volume if past the aortic valve | Curved, flat volume, shell-like | Curved, flat volume, maybe some protrusions in map, outline of the diaphragm on inferior side |
| Voltage map | High voltage areas | High voltage areas | Low voltage | High voltage areas | Low voltage |
| Impedance of tissue | Typical cardiac tissue | Typical cardiac tissue | Higher impedance | Higher impedance | Higher impedance |

Embodiment 1: Advancement of Wire for Trajectory

After puncture, the wire will be advanced into the free space. The representation of the device on the EAM system, and how it advances into the new space (for example, a dot, or a device with more than one electrode) will provide the operator with information about the space. (See, for example, Table 1, FIGS. 2A-2E). In some embodiments, a single dot will be visualized by the EAM system for a wire (or device) with one electrode, and a wire (or device) with multiple electrodes will be displayed as multiple points joined together by a tube, or as a series of dots.

Referring to FIGS. 1 and 2A-2E, after entry into new space, insulation 212 is moved relative to the mechanical puncture feature 210 to expose the correct length of conductive material (e.g., metal) to function as an electrode for imaging.

Anatomy shown in FIGS. 2A-2E includes left atrium 100, right atrium 102, pericardial space 104, aorta 106, left ventricle 108, right ventricle 110, inferior vena cava 112, superior vena cava 114, lung 116, and diaphragm 118. FIGS. 2A-2E also includes introducer device 200 and puncture device tip 202. Examples of introducer device 200 include a sheath, dilator, catheter, or assembly that has electrodes 140, and is thus visualizable on the EAM system. The electrodes 140 of the introducer device 200 shown in FIGS. 2A-2E are arranged in a linear configuration. The puncture device tip 202 of FIGS. 2A-2E is the visualization/representation of a single electrode device on the EAM system. The mechanical puncture feature 214 of mechanical puncture wire 210 (FIG. 1) would be visualized as puncture device tip 202 on an EAM system.

Figure 2A:
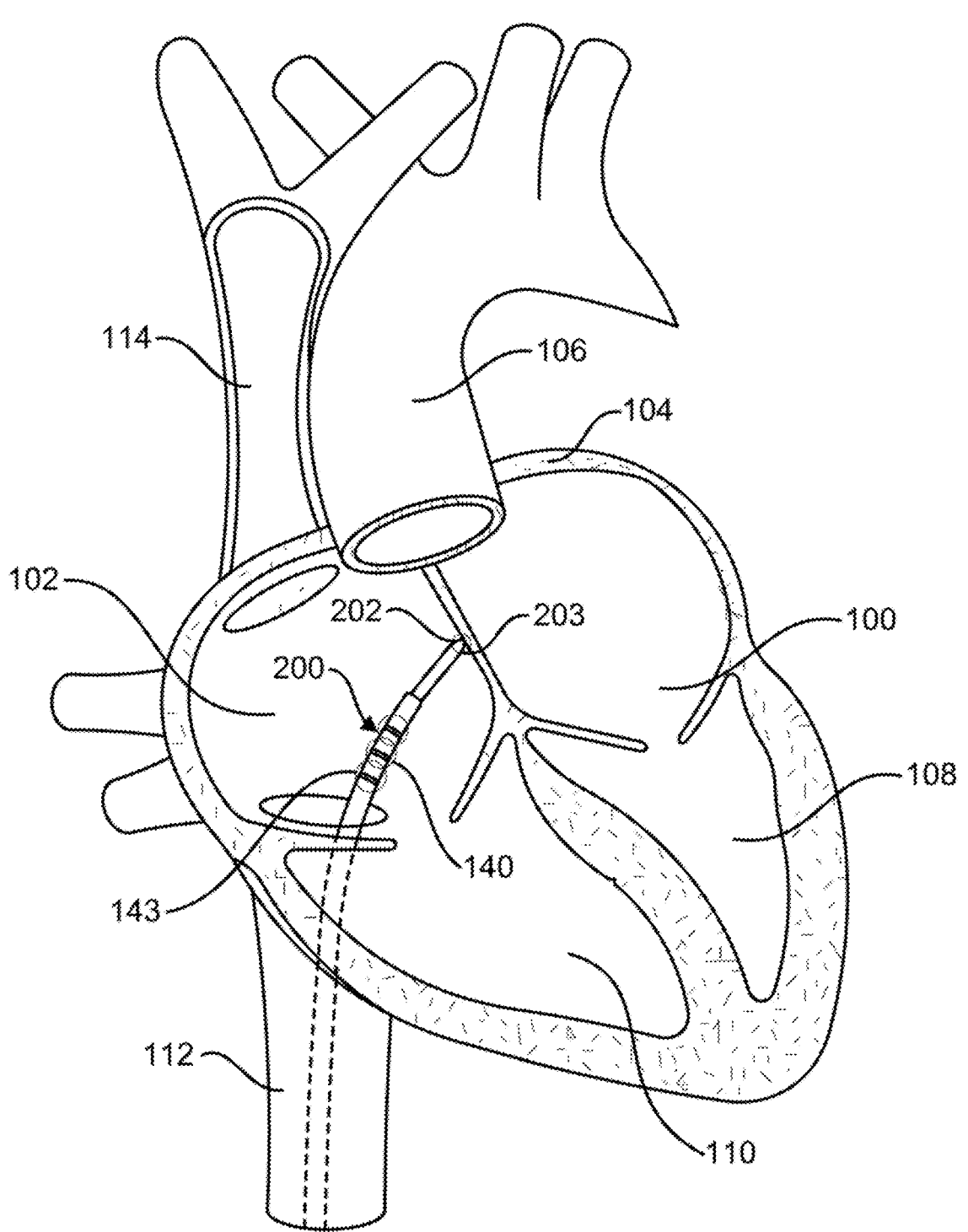
FIGS. 2A-2E illustrate a puncture device being advanced through anatomy.
Figure 2B:
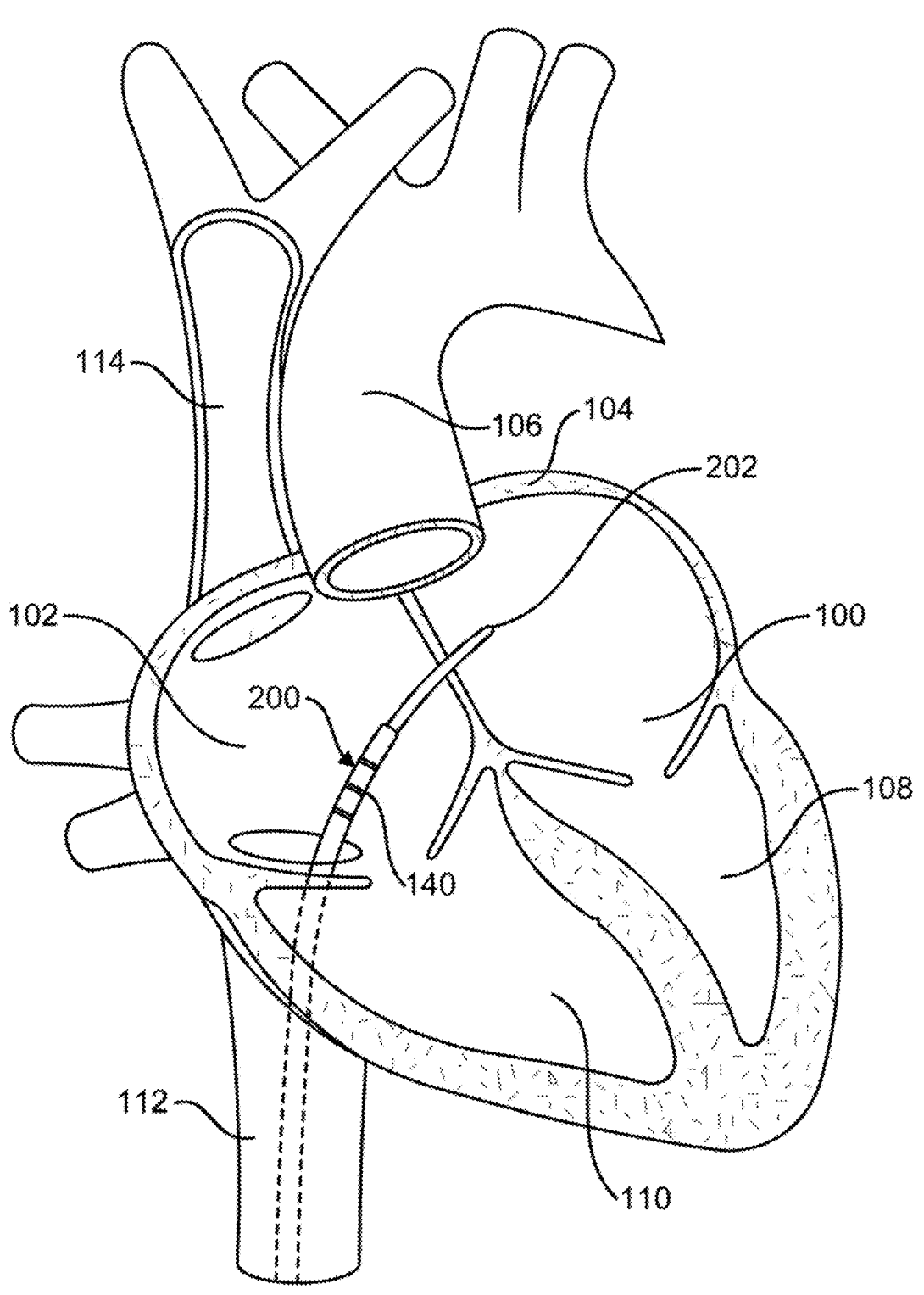
Figure 2C:
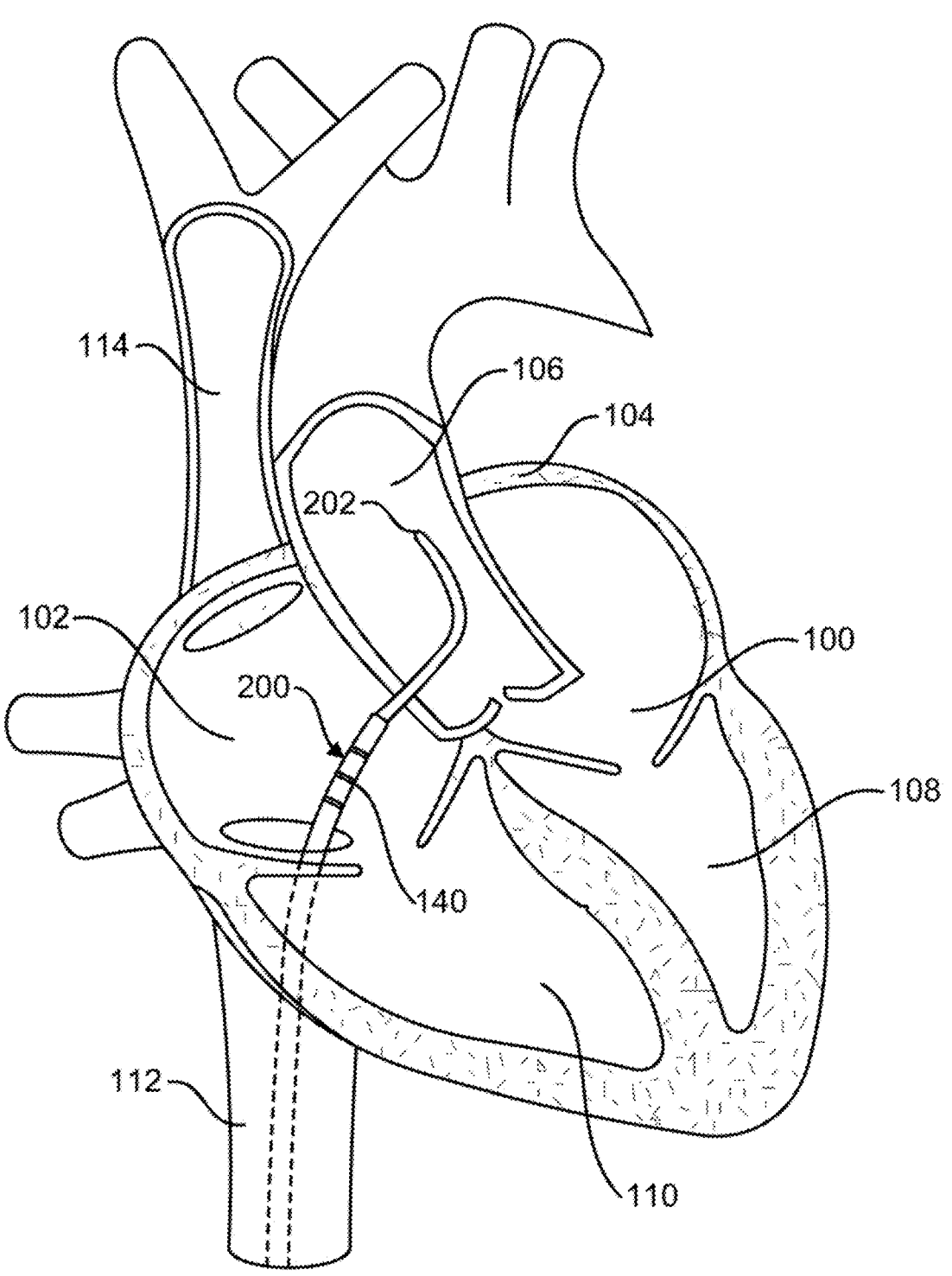
Figure 2D:
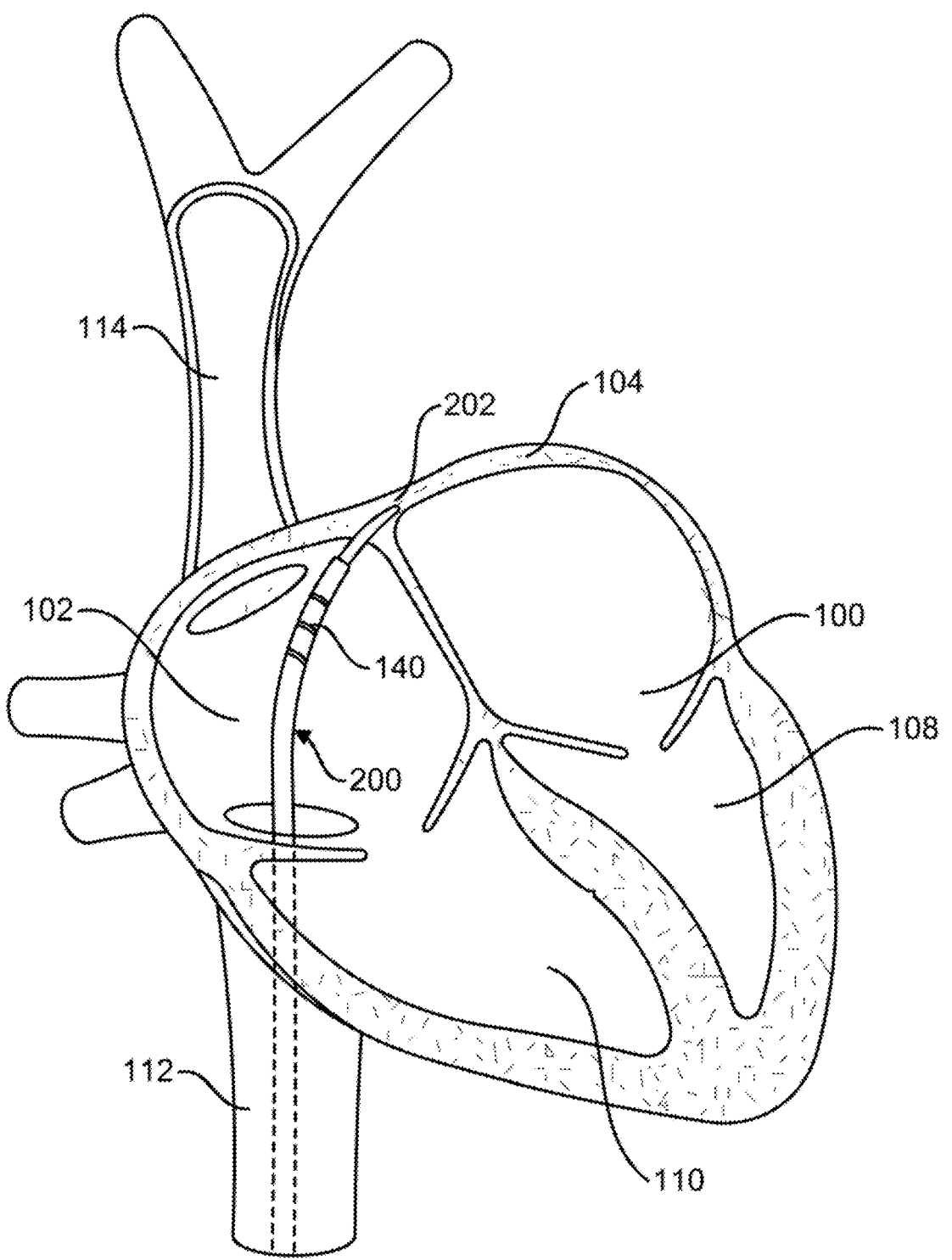
Figure 2E:
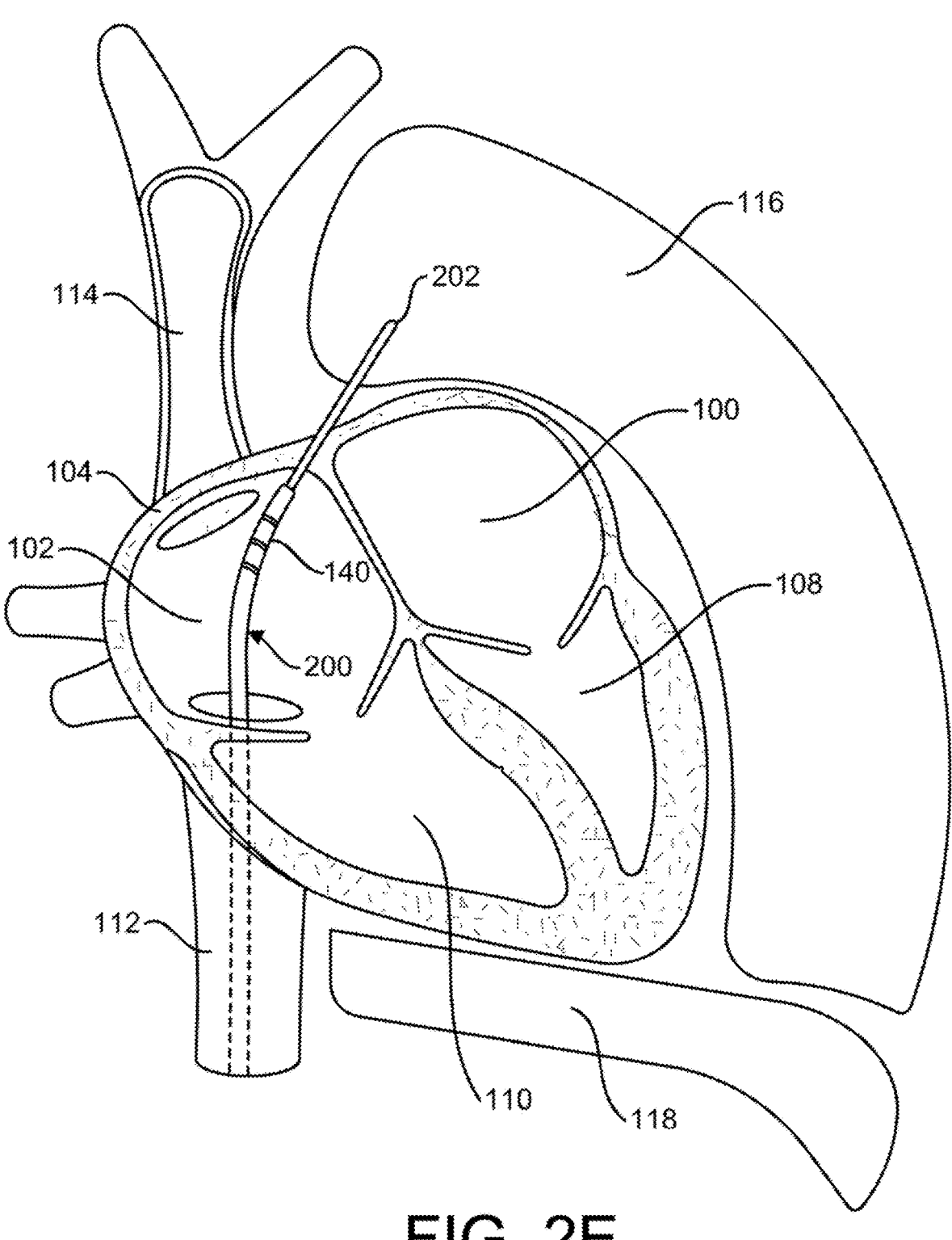

Puncture device tip 202, which may be represented as a dot 203 on the monitor of an EAM system, is shown as a dot 203 in FIG. 2A. Electrodes 140 may also be shown as a series of dots 143, optionally as points joined together by a tube. FIG. 2A shows puncture device tip 202 tip in right atrium 102. FIG. 2B shows puncture device tip 202 tip in left atrium 100. FIG. 2C shows puncture device tip 202 tip in aorta 106. FIG. 2D shows puncture device tip 202 tip in pericardial space 104, and FIG. 2E shows puncture device tip 202 tip external to the pericardium. Volumes external to the pericardium include lung 116 and diaphragm 118.

For example, advancement into the aorta may cause the wire representation (either dot, vector or curve) to travel superiorly, or inferiorly and/or anteriorly in the left ventricle, and the wire would not travel to the anatomical left, or right on the EAM visualization.

Additional information may be gathered if there are more than one electrode on the device in the new space. More than one electrode will allow the wire to be visualized as a vector or curve on the EAM system. If the wire has shape-memory properties, any deformation to the expected shape may provide additional information about the shape of the chamber.

Embodiment 2: Mapping

If the wire and EAM system are able to generate a map, the generation of a FAM or voltage map will give the operator information about the newly entered space. In some aspects, the device tip 202 is used to generate the FAM or voltage map in a newly entered space. In some aspects, the electrodes 140 of the introducer device 200 can be used to generate the FAM or voltage map in a newly entered space.

To more easily create and characterize the volume, a steering mechanism for the distal end of the device (to increase the degrees of freedom from 2 degrees of freedom) may be beneficial. The volumes and relative location from a reference in the right atrium (e.g., visualized device in the right atrium, tags from anatomical features like the "His bundle", or a right atrial map) may inform the operator of the newly entered space (Table 1, FIG. 3, FIG. 4).

Figure 3:
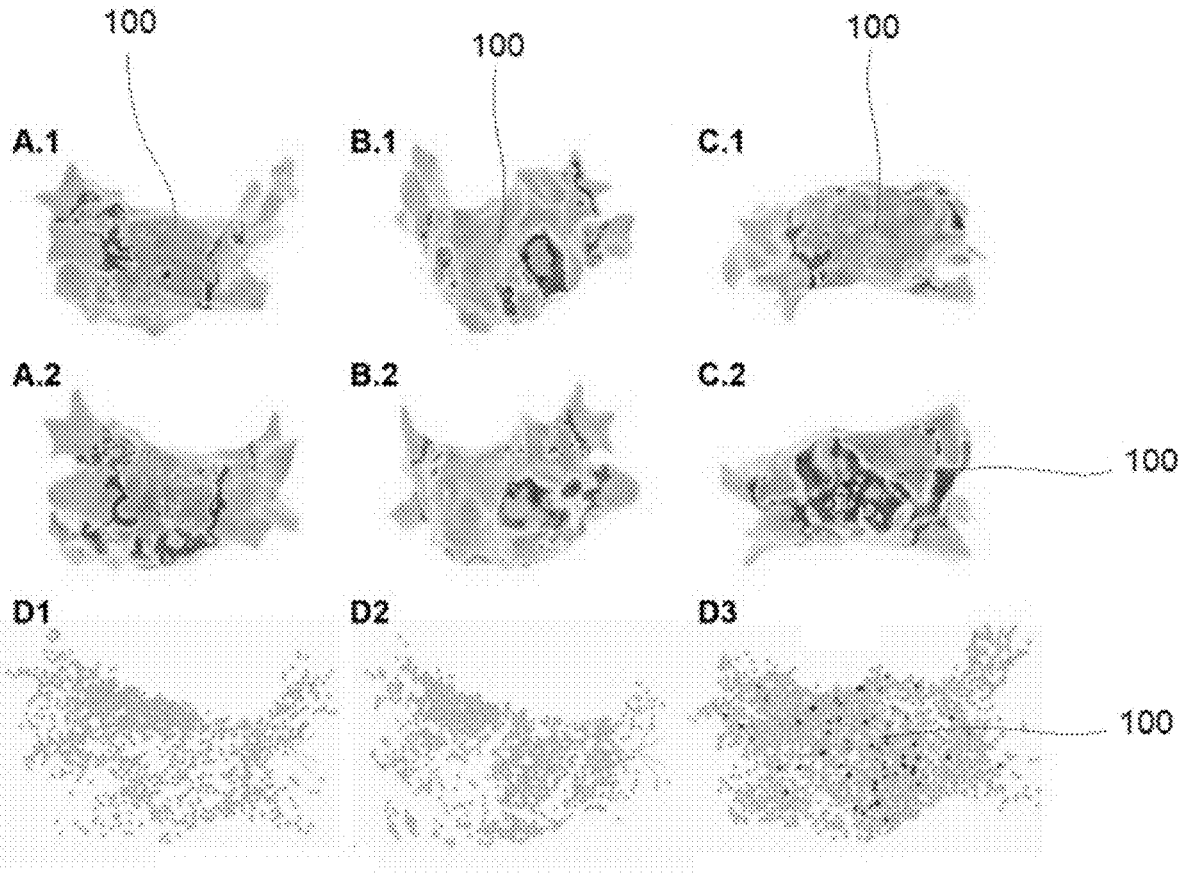
FIG. 3 is an illustration of different mappings of a left atrium.

FIG. 3 shows examples of mappings of left atrium 100 as discussed in "Validating Left Atrial Low Voltage Areas During Atrial Fibrillation and Atrial Flutter Using Multi-electrode Automated Electroanatomic Mapping" by Rodriguez-Manero et al., JACC: Clinical Electrophysiology, Volume 4, Issue 12, 2018.

Figure 4:
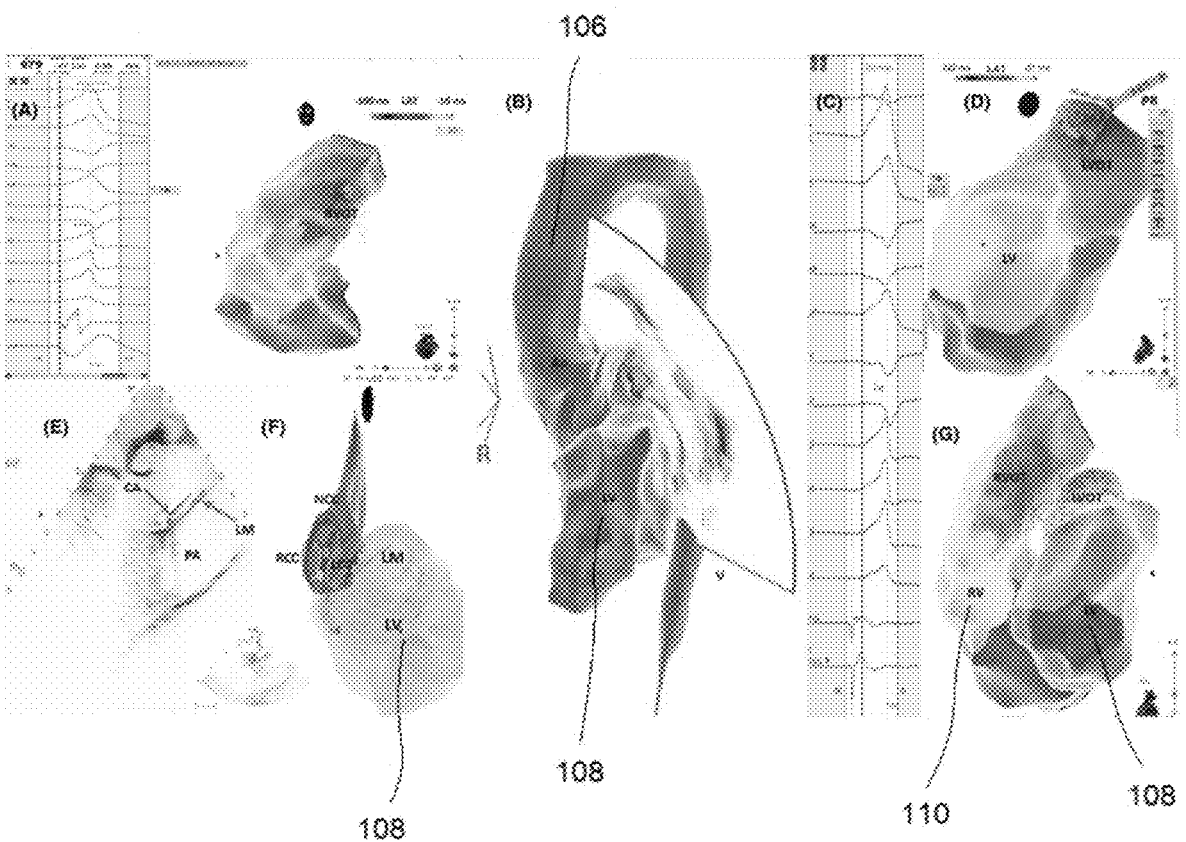
FIG. 4 is an illustration of mappings of heart anatomy, including an aorta.

FIG. 4 is an illustration of mappings of heart anatomy, including an aorta as discussed in "Zero-fluoroscopy catheter ablation of premature ventricular contractions at left coronary cusp near left main coronary artery" by Santoro et al., Clinical Case Reports, 2020. FIG. 4 includes aorta 106, left ventricle 108, and right ventricle 110.

A voltage map may help identify if the region is not in contact with the myocardium, for example if the device is extrapericardial or in the aorta. In these regions, the voltage map would show areas of low voltage.

A full map of the space or chamber may not be required to identify the space. An operator may look for specific characteristics to avoid creating a full map of the chamber which would otherwise be time consuming.

Voltage mapping requires the electrodes of the wire to come in contact with the tissue.

Embodiment 3: Tissue Impedance

The different tissue types have different impedances. Electrodes on the device would be required to contact the tissue. A system (in the EAM system, or another device like an RF generator) would be able to provide information to the operator about the tissue qualities. Myocardium would have a different impedance (lower) than aorta and tissue outside of the pericardium (See, for example, Table 1).

A device (e.g., wire or microcatheter) suitable for facilitating the aforementioned three embodiments preferably includes at least one distal electrode that is electrically continuous along the electrode's length, and connectable to an electrical recording system (e.g., EAM system, pacing system) outside of the body. The remainder of the device length should remain electrically insulated. By way of example, in the case of a wire, the distal electrode may be an exposed, uninsulated portion of the wire's core body which is electrically conductive. In another example, in the case of a microcatheter or a wire, the distal electrode may be a distinct component from the wire's core body and is connected to an electrical wire that travels the length of the device to exit the body. The electrode length can range from 0.5 mm to 3 mm. For accurate tracking of the electrode position, the distal electrode should be approximately 0.75 mm to 1.5 mm in length.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

PARTS left atrium 100, right atrium 102
pericardial space 104
aorta 106
left ventricle 108, right ventricle 110
inferior vena cava 112, superior vena cava 114
lung 116
diaphragm 118
introducer device 200 (e.g., a sheath, dilator, catheter, or assembly that has electrodes, and is thus visualizable on the EAM system)
puncture device tip 202
mechanical puncture wire 210
insulation 212
mechanical puncture feature 214
handle 216

We claim:

1. A method of puncturing a target tissue and evaluating an anatomical space, the method comprising the steps of:
   (a) puncturing the target tissue with an elongate puncture device to create a puncture;
   (b) advancing a distal tip of the elongate puncture device through the puncture and into the anatomical space;
   (c) evaluating a shape of the anatomical space using the elongate puncture device connected to an electroanatomic mapping (EAM) system;
   (d) identifying the anatomical space based on the evaluated shape; and
   (e) determining whether the identified anatomical space is a desired anatomical space or an unintended anatomical space.

2. The method of claim 1, wherein step (c) includes using the distal tip of the elongate puncture device to evaluate the anatomical space.

3. The method of claim 1, further comprising a step of (f) withdrawing the elongate puncture device and repeating steps (a) to (e) until a desired anatomical space is identified.

4. The method of claim 1, further comprising a step of (f), when a desired anatomical space is identified, of advancing a dilator over the elongate puncture device to dilate the puncture.

5. The method of claim 4, further comprising a step of (g) advancing a sheath over the dilator.

6. The method of claim 1, wherein the elongate puncture device is a wire, a microcatheter, or a needle.

7. The method of claim 1, wherein the elongate puncture device has a sharp tip for mechanical puncturing.

8. The method of claim 1, wherein the elongate puncture device has an electrode for delivering electrical energy for puncturing.

9. The method of claim 1, wherein step (b) includes the elongate puncture device being electrically connected to the EAM system while the elongate puncture device is being advanced.

10. The method of claim 1, wherein the anatomical space is identified to be a left atrium, an aorta, a pericardial space, or a thoracic cavity which is extrapericardial.

11. A method of puncturing a target tissue and evaluating an anatomical space, the method comprising the steps of:

(a) puncturing the target tissue with an elongate puncture device to create a puncture;

(b) advancing a distal tip of the elongate puncture device through the puncture and into the anatomical space;

(c) evaluating a quality of the anatomical space using the elongate puncture device connected to an electroanatomic mapping (EAM) system;

(d) identifying the anatomical space based on the evaluated quality; and (e) determining whether the identified anatomical space is a desired anatomical space or an unintended anatomical space.

12. The method of claim 11, wherein the quality being evaluated is voltage or impedance of tissue in the anatomical space as measured by the elongate puncture device.

13. The method of claim 11, wherein step (c) includes using the distal tip of the elongate puncture device to evaluate the anatomical space.

14. The method of claim 11, further comprising a step of (f) withdrawing the elongate puncture device and repeating steps (a) to (e) until a desired anatomical space is identified.

15. The method of claim 11, further comprising a step of (f) when a desired anatomical space is identified, of advancing a dilator over the elongate puncture device to dilate the puncture.

16. The method of claim 15, further comprising a step (g) advancing a sheath over the dilator.

17. The method of claim 11, wherein the elongate puncture device is a wire, microcatheter, or needle.

18. The method of claim 11, wherein the elongate puncture device has a sharp tip for mechanical puncturing.

19. The method of claim 11, wherein the elongate puncture device has an electrode for delivering electrical energy for puncturing.

20. The method of claim 11, wherein the anatomical space is identified to be a left atrium, an aorta, a pericardial space, or a thoracic cavity which is extrapericardial.

\* \* \* \* \*